United States Patent [19]
Samejima et al.

[11] Patent Number: 4,581,472
[45] Date of Patent: Apr. 8, 1986

[54] PROCESS FOR PREPARING A PERFLUOROACRYLIC ACID ESTER

[75] Inventors: Shunichi Samejima, Tokyo; Isamu Kaneko, Yamato, both of Japan

[73] Assignee: Asahi Glass Company Ltd., Tokyo, Japan

[21] Appl. No.: 543,296

[22] Filed: Oct. 19, 1983

[30] Foreign Application Priority Data

Nov. 9, 1982 [JP] Japan .................................. 57-195264

[51] Int. Cl.$^4$ ..................... C07C 67/317; C07C 67/14
[52] U.S. Cl. ..................................... 560/211; 560/210
[58] Field of Search ................ 560/211, 210, 183, 184

[56] References Cited

U.S. PATENT DOCUMENTS 4,153,804  5/1979  Yamabe et al. ..................... 560/184
4,358,412 11/1982  Ezzell et al. ......................... 560/183

OTHER PUBLICATIONS

LaZerte, J. D. et al., J. Am. Chem. Soc. vol. 75 (1953) pp. 4525–4528.
Haszeldine, R. N., J. Chem. Soc. (1954) pp. 4026–4028.

Primary Examiner—Natalie Trousof
Assistant Examiner—L. Hendriksen
Attorney, Agent, or Firm—Oblon, Fisher, Spivak, McClelland & Maier

[57] ABSTRACT

A process for producing a perfluoroacrylic acid ester represented by the general formula $CF_2=CFCOOR$ where R is a monovalent organic substituent, which comprises pyrolyzing a monoester of perfluorosuccinyl fluoride represented by the general formula $FOCCF_2CF_2COOR$ where R is as defined above, in a vapor phase.

7 Claims, No Drawings

PROCESS FOR PREPARING A PERFLUOROACRYLIC ACID ESTER

The present invention relates to a process for preparing a perfluoroacrylic acid ester.

A perfluoroacrylic acid ester (i.e. $CF_2=CFCOOR$ where R is an organic substituent) is a substance useful as a starting material for a polymer having a —COOR group or a group derived therefrom on its side chain, or as an intermediate for various fluorinated compounds.

The following processes have been known for the preparation of such a substance:

(1) a process wherein carbon tetrachloride or trichlorofluoromethane is added to chlorotrifluoroethylene or 1,2-dichlorodifluoroethylene as a starting material to obtain 1,1,2-trifluoropentachloropropane, which is then oxidized and esterified to form a 2,3-dichlorotrifluoropropanoic acid ester, followed by dechlorination of the ester;

(2) a process wherein bromine is added to chlorotrifluoroethylene to obtain 1,2-dibromo-1-chlorotrifluoroethylene, which is then subjected to an addition reaction with propylene, followed by dehydrobromination to obtain 5-bromo-4-chloro-4,5,5-trifluoropentene-2 ($CF_2BrCFClCH=CHCH_3$), which is then oxidized and esterified to form a 3-bromo-2-chlorotrifluoropropanoic acid ester, which is in turn dehalogenated; and (3) a process wherein chlorotrifluoroethylene is subjected to an addition reaction with hydrogen bromide, followed by dehalogenation to obtain trifluoroethylene, which is then subjected to an addition reaction with ICl, followed by dehydrochlorination to obtain trifluoroiodoethylene, which is then reacted with metal magnesium in ether to form an organomagnesium intermediate, which is in turn reacted with carbon dioxide, followed by hydrolysis to obtain perfluoroacrylic acid, which is then esterified.

However, these conventional processes require multiple reaction steps to obtain the desired substance and include some reaction steps where yields are low. Thus, these processes have drawbacks that they require cumbersome operations and the total yield of the desired substance is extremely low.

The present inventors have conducted extensive researches to overcome such drawbacks and have finally found that it is possible to obtain a perfluoroacrylic acid ester in good yield by pyrolyzing in a vapour phase a monoester of perfluorosuccinyl fluoride which can be readily prepared in good yield by a three-step reaction from tetrafluoroethylene as the starting material. The present invention has been accomplished based on this discovery.

Thus, present invention provides a novel process for producing a perfluoroacrylic acid ester represented by the general formula $CF_2=CFCOOR$ where R is a monovalent organic substituent, which comprises pyrolyzing a monoester of perfluorosuccinyl fluoride represented by the general formula $FOCCF_2CF_2COOR$ where R is as defined above, in a vapour phase.

Now, the present invention will be described in detail with reference to the preferred embodiments.

The monoester of perfluorosuccinyl fluoride to be used as the starting material in the present invention, can be prepared in good yield, for instance, by a process which comprises reacting an alcohol represented by the general formula ROH with perfluoro--butyrolactone or perfluorosuccinyl difluoride or a mixture thereof, which is obtainable, for instance, by oxidation of 1,4-diiodooctafluorobutane which is in turn obtainable from the reaction of tetrafluoroethylene with iodine (see Japanese Unexamined Patent Publications No. 59111/1977 and No. 40708/1978).

The organic substituents R in the above-mentioned monoester is preferably a straight, branched or cyclic alkyl group having from 1 to 10, particularly from 1 to 5, carbon atoms, in view of the usefulness of the final product and the operability of the process.

In the present invention, the monoester is pyrolyzed in a vapour phase, preferably in the presence of a solid medium such as powder or bead of an alkali metal carbonate, zinc oxide or glass. The reaction temperature is properly selected depending upon e.g. the type of the starting material, and is usually within a range of from 150° to 500° C., preferably from 200° to 450° C., more preferably from 300° to 400° C. In a normal operation of the reaction, the starting material monoester is introduced as a vapour into the reactor and pyrolyzed at a temperature within the above-mentioned range. The residence time may be selected within a wide range of from 1 to 300 seconds. In general, however, the residence time may be shortened as the reaction temperature becomes higher. When the reaction temperature is too low or the residence time is too short, the conversion of the starting material tends to be low, and if the reaction temperature is too high or the residence time is too long, a side reaction tends to increase. In each case, the yield of the desired product tends to be low. It is preferred to employ a residence time of from 5 to 30 seconds.

Furthermore, the reaction of the present invention is preferably conducted in the presence of an inert gas such as nitrogen, helium or argon, as a diluent to suppress side reactions. For instance, it is preferred to conduct the reaction in the presence of a diluent at a molar ratio of the inert gas to the starting material gas of from 50/50 to 99/1, preferably from 70/30 to 95/5. It is of course possible to preliminarily vaporize the starting monoester prior to its introduction into the reaction zone. In case of a high boiling starting material, it may directly be introduced into the reaction zone without such preliminary vaporization, and the pyrolysis is conducted simultaneously with the vaporization of the starting material. For instance, the starting material monoester may preliminarily be vaporized and mixed with an inert gas so that it is introduced into the reaction zone in the form of a mixture with the inert gas, or the starting material and the inert gas may independently be introduced into the reaction zone so that the reaction is conducted under a diluted condition.

In the present invention, various types of the reactor may optionally be employed, such as an empty tower, a packed tower or a fluidized bed reactor. However, from the viewpoints of suppressing the side reactions and increasing the reactor efficiency, it is preferred to employ a fluidized bed reactor.

In the process of the present invention, carbonyl fluoride which will be produced in an equimolar amount to the desired substance, has a boiling point which is substantially different from the boiling point of the desired substance, and accordingly it may readily be separated from the desired substance simply by leaving the reaction product in a cold trap at room temperature. Further, unreacted starting material or by-products such as perfluorosuccinic acid diester and perfluorosuccinic anhydride derived from side reactions, which may remain in the reaction product, may also be separated readily by a usual separating means such as distilaltion.

Now, the present invention will be described in further detail with reference to the Examples. However, it should be understood that the present invention is by no means restricted by such specific examples.

EXAMPLE 1

Into a stainless steel fluidized bed having an internal diameter of 47 mm and a length of 450 mm, 640 g of glass beads having an average particle size of 100 m (GB 736 manufactured by Toshiba Glass Beads) were packed to a height of 240 mm. While supplying nitrogen gas at a rate of 1.1 liter/min (20° C.), the fluidized bed was heated to 370° C. and fluidized, and then 880 g of monomethylester of perfluorosuccinyl fluoride ($FOCCF_2CF_2COOCH_3$) was supplied to the fluidized bed at a rate of 120 g/hr, whereby the pyrolysis was conducted. During the reaction, the flow velocity was 2.7 cm/sec, and the residence time was about 9 seconds. The reaction product discharged from the outlet of the fluidized bed was collected directly in a series of traps cooled to a temperature of $-78°$ C. and $-196°$ C. The reaction product was analyzed by gas chromatography and $^1H$, $^{19}F$ NMR spectroscopy.

The conversion of the monomethylester was 89%, and the selectivity of the desired methylperfluoroacrylate was 75%. Further, the production rates of dimethylperfluorosuccinate and perfluorosuccinic anhyhdride as by-products were 21% and 4%, respectively.

EXAMPLE 2

The operation was conducted in the same manner as in Example 1 except that the reaction temperature was 320° C., the flow rate of the nitrogen gas was 1.2 liter/min (20° C.) and 400 g of the monomethylester of perfluorosuccinyl fluoride was fed at a rate of 100 g/hr, whereby the conversion of the monomethylester was 68% and the selectivity of methylperfluoroacrylate was 59%.

EXAMPLE 3

The operation was conducted in the same manner as in Example 1 except that instead of the monomethylester, 260 g of a monoethylester ($FOCCF_2CF_2COOCH_2CH_3$) was fed at a rate of 130 g/hr, whereby the conversion of the monoethylester was 75% and the selectivity of the desired ethylperfluoroacrylate ($CF_2=CFOOCH_2CH_3$) was 70%. Further, the production rates of diethylperfluorosuccinate and perfluorosuccinic anhyhdride as by-products were 22% and 8%, respectively.

EXAMPLE 4

The operation was conducted in the same manner as in Example 1 except that the reaction temperature was 390° C., the flow rate of nitrogen gas was 1.2 liter/min (20° C.) and 110 g of a monopentylester of perfluorosuccinyl fluoride ($FOCCF_2CF_2COOC_5H_{11}$) was fed at a rate of 56 g/hr, whereby the conversion of the monopentylester was 92% and the selectivity of pentylperfluoroacrylate was 56%.

We claim:

1. A process for producing a perfluoroacrylic acid ester represented by the formula $CF_2=CFCOOR$ where R is a monovalent organic substituent, which comprises pyrolyzing a monoester of perfluorosuccinyl fluoride represented by the formula $FOCCF_2CF_2COOR$ where R is as defined above, in a vapour phase.

2. The process according to claim 1, wherein the pyrolysis is conducted at a temperature of from 300° to 400° C.

3. The process according to claim 1, wherein the pyrolysis is conducted in the presence of an inert gas as a diluent.

4. The process according to claim 3 wherein the molar ratio of the inert gas to the monoester is from 70/30 to 95/5.

5. The process according to claim 1, wherein R is an alkyl group having from 1 to 5 carbon atoms.

6. The process according to claim 1, wherein the pyrolysis is conducted in the presence of a solid medium in the form of powder or bead.

7. The process according to claim 6, wherein the solid medium is glass bead.

* * * * *